(12) United States Patent
Rom

(10) Patent No.: US 8,396,550 B2
(45) Date of Patent: Mar. 12, 2013

(54) OPTIMAL CARDIAC PACING WITH Q LEARNING

(75) Inventor: Rami Rom, Zichron Yaacov (IL)

(73) Assignee: Sorin CRM SAS, Clamart (FR)

( * ) Notice: Subject to any disclaimer, the term of this patent is extended or adjusted under 35 U.S.C. 154(b) by 19 days.

(21) Appl. No.: 13/126,199

(22) PCT Filed: Oct. 29, 2009

(86) PCT No.: PCT/IL2009/001009
§ 371 (c)(1),
(2), (4) Date: Apr. 27, 2011

(87) PCT Pub. No.: WO2010/049931
PCT Pub. Date: May 6, 2010

(65) Prior Publication Data
US 2011/0213435 A1 Sep. 1, 2011

Related U.S. Application Data

(60) Provisional application No. 61/109,194, filed on Oct. 29, 2008.

(51) Int. Cl.
*A61N 1/36* (2006.01)
(52) U.S. Cl. .......................................... 607/4
(58) Field of Classification Search ............ 607/4–5
See application file for complete search history.

(56) References Cited

U.S. PATENT DOCUMENTS

| 3,833,865 | A | 9/1974 | Palmer |
|---|---|---|---|
| 5,692,907 | A | 12/1997 | Glassel et al. |
| 5,800,471 | A | 9/1998 | Baumann |
| 6,366,813 | B1 | 4/2002 | DiLorenzo |
| 6,459,929 | B1 | 10/2002 | Hopper et al. |
| 6,484,059 | B2 | 11/2002 | Gielen |
| 7,006,872 | B2 | 2/2006 | Gielen et al. |
| 7,209,787 | B2 | 4/2007 | DiLorenzo |
| 7,231,254 | B2 | 6/2007 | DiLorenzo |
| 7,242,984 | B2 | 7/2007 | DiLorenzo |
| 7,441,429 | B1 | 10/2008 | Nucci et al. |
| 2003/0204368 | A1 | 10/2003 | Ertin et al. |
| 2004/0260560 | A1 | 12/2004 | Holloway et al. |
| 2005/0202384 | A1 | 9/2005 | DiCuccio et al. |
| 2006/0235477 | A1 | 10/2006 | Rom |
| 2007/0143851 | A1 | 6/2007 | Nicodemus et al. |
| 2007/0177615 | A1 | 8/2007 | Miliefsky |

(Continued)

FOREIGN PATENT DOCUMENTS

| WO | 01/95293 A2 | 12/2001 |
|---|---|---|
| WO | 2005007075 A2 | 1/2005 |

(Continued)

OTHER PUBLICATIONS

International Search Report for PCT/IL2009/001009 issued Feb. 5, 2010 by European Patent Office as ISA.

(Continued)

*Primary Examiner* — Scott Getzow
*Assistant Examiner* — Amanda Patton
(74) *Attorney, Agent, or Firm* — Simon Kahn; Chanoch Kahn

(57) ABSTRACT

A cardiac pacemaker control system constituted of: a means for receiving input from a hemodynamic sensor; an adaptive control system in communication with the means for receiving input from the hemodynamic sensor; and an interface arranged to provide cardiac stimulation responsive to the adaptive control system; the adaptive control system comprising a learning module operative to converge to patient specific cardiac pacing stimulation timing using a machine learning scheme in cooperation with a probabilistic replacement scheme, the probabilistic replacement scheme arranged to replace inputs from the hemodynamic sensor with online calculated values.

17 Claims, 8 Drawing Sheets

U.S. PATENT DOCUMENTS

| | | | |
|---|---|---|---|
| 2008/0052401 A1 | 2/2008 | Bugenhagen et al. |
| 2008/0052541 A1 | 2/2008 | Ginter et al. |
| 2008/0072322 A1 | 3/2008 | Guruswamy |
| 2008/0240128 A1 | 10/2008 | Elrod |

FOREIGN PATENT DOCUMENTS

| | | | |
|---|---|---|---|
| WO | 2006/017277 A2 | 2/2006 |
| WO | 2006061822 A2 | 6/2006 |
| WO | 2008010220 A2 | 1/2008 |

OTHER PUBLICATIONS

Written Opinion of the International Searching Authority for PCT/IL2009/001009 issued Feb. 5, 2010 by European Patent Office as ISA.

Whinnett, Z.I. et al; "Haemodynamic Effects of Changes in AV and VV Delay in Cardiac Resynchronisation Therapy Show a Consistent Pattern: Analysis of Shape, Magnitude and Relative Importance of AV and VV Delay"; Published online by Heart May 18, 2006.

Watkins and Dayan; "TEchnical Note: Q-Learning"; published 1992 in Machine Learning, pp. 279-292, Boston, MA.

Rom et al; "Adaptive Cardiac Resynchronization Therapy Device: A Simulation Report"; published Nov. 2005, PACE, vol. 28, pp. 1168-1173.

Rom et al: "Adaptive Cardiac Resynchronization Therapy Device Based on Spiking Neurons Architecture ADN Reinforcement Learing Scheme"; Mar. 2, 2007, IEEE Transactions on Neural Networks, vol. 18, No. 2, pp. 542-550; IEEE New York, NY.

International Search Report for PCT/IL2009/001071 issued Mar. 19, 2010 by USPTO as ISA.

Written Opinion of the International Searching Authority for PCT/IL2009/001071 issued Mar. 19, 2010 by USPTO as ISA.

Kaelbling, L.P. et al; "Reinforcement Learning: A Survey"; Journal of Artificial Intelligence Research 4 (1996); pp. 237-285; AI Access Foundation and Morgan Kaufmann Publishers.

Whinnett, B.M. et al; "The Atrioventricular Delay of Cardiac Resynchronization Can Be Optimized Hemodynamically During Exercise and Predicted From Resting Measurements"; Journal of Heart Rhythm vol. 5, No. 3, Mar. 2008; pp. 378-386; Heart Rhythm Society.

Zuber, M. et al; "Comparison of Different Approaches for Optimization of Atrioventricular and Interventricular Delay in Biventricular Pacing"; Europace (2008) 10, pp. 367-373; European Society of Cardiology.

O'Donnell, D. et al: "Long-Term Variations in Optimal Programming of Cardiac Resynchronization Therapy Devices"; PACE, vol. 28, Jan. 2005, Supplement I, pp. S24-S26.

OPTIMAL CARDIAC PACING WITH Q LEARNING

BACKGROUND OF THE INVENTION

The invention relates generally to closed loop control systems, and more particular to a machine learning controller for medical devices exhibiting automatic optimization of cardiac pacemakers and ICD devices stimulations using a machine learning scheme.

Implanted pacemakers and intracardiac cardioverter defibrillators (ICD) deliver therapy to patients suffering from various heart-diseases. Congestive heart failure (CHF) is defined generally as the inability of the heart to deliver enough blood to meet the metabolic demand. Often CHF is caused by electrical conduction defects. The overall result is a reduced blood stroke volume from the left side of the heart. Since it is known that cardiac output depends strongly on the left heart contraction in synchrony with the right heart, as described inter alia in U.S. Pat. No. 6,223,079, issued Apr. 24, 2001 to Bakels et al, entitled "Bi-Ventricular Pacing Method", the entire contents of which is incorporated herein by reference, CHF patients are often implanted with a bi-ventricular pacemaker with electrodes in 3 chambers. The bi-ventricular pacemaker is arranged to re-synchronize the left heart contraction to the right heart contraction, resulting in an effective therapy. The resynchronization task demands exact pacing management, primarily focused on accurate timing, of the heart chambers such that the overall stroke volume is maximized for a given heart rate (HR), where it is known that the key point is to bring the left ventricle to contract in synchrony with the right ventricle. The re-synchronization task is patient and activity dependent, and thus for each patient the best combination of pacing time intervals which results in restored synchrony varies during the normal daily activities of the patient.

The positioning of the implanted leads in the right and left ventricles are another important contributor to the success of CRT devices and in World Intellectual Property Organization Patent Publication WO2006/0016822, published to ROM on Jun. 15, 2006 entitled "Optimizing and Monitoring Cardiac Resynchronization Therapy Devices", the entire contents of which are incorporated herein by reference, a method to find and validate optimal lead positioning in implantation based on the adaptive CRT control system is described.

Q-learning (QL) is a reinforcement learning technique that works by learning an action-value function that gives the expected utility of taking a given action in a given state and following a fixed policy thereafter. One of the strengths of Q-learning is that it is able to compare the expected utility of the available actions without requiring a model of the environment. Watkins and Dayan in an article entitled "Q Learning", published 1992 in Machine Learning 8, 279-292, 1992, showed that online solution of a QL recursive formula is guaranteed to converge to the optimal policy in a model free reinforcement learning problem.

D. Odonnell et al reported in "Long-Term Variations in Optimal Programming of Cardiac Resynchronization Devices", published in PACE 28; Jan. 2005; 24-26, the results of a clinical study with 40 CHF patients. The authors found that the optimal atrio-ventricular (AV) delay and inter-ventricular (VV) interval, obtained using echocardiography, varied significantly during 9 months of patient follow-ups. The authors explained the results by a slow and gradient improvement in the cardiac function due to implanted cardiac resynchronization therapy (CRT) devices that generated a reverse remodeling of the left ventricle.

Whinnett et al in "Haemodynamic Effects of Changes in AV and VV Delay in Cardiac Resynchronization Therapy Show a Consistent Pattern: Analysis of Shape, Magnitude and Relative Importance of AV and VV delay", published online in Heart, 18 May 2006, doi:10.1136/hrt.2005.080721", has studied the dependence on AV and VV timings in CRT patients using non-invasive systolic blood pressure (SBP) measurements. The authors propose a Gaussian fit for the measured SBP as a function of AV and VV such that the maximum SBP value is at the optimal AV and VV delay timings specific for each CRT patient. Whinnett et al reports that in higher heart rates, produced with higher rate atrial pacing, the response to variations in AV and VV timings is more significant and hence the Whinnett Gaussian fit surface is usually obtained with higher heart rates.

Whinnett et al in "The Atrioventricular Delay of Cardiac Resynchronization Can be Optimized Hemodynamically During Exercise and Predicted from Resting Measurements" published 2008 in Heart Rhythm, Vol. 5, pages 378-386, showed that CRT patients are more symptomatic at high heart rates and hence it is important to optimize the CRT device both at rest condition and at higher heart rates. The authors further propose a method to calculate optimal AV delay and VV interval timing during exercise using measurements in rest mode, normal sinus rhythm and atrial pacing with higher rates.

The proposal by Whinnett is a Guassian fit obtained offline with post processing averaging of the measured SBP data after calculating an average over several cardiac cycles before a pacing configuration change is made. The actual SBP data obtained is noisy and does not easily show the underlying surface.

Michel Zuber et al in "Atrioventricular and Interventricular Delay in BiVenricular Pacing", published January 2008 on-line on behalf of the European Society of Cardiology, using an external non-invasive heart sound method, show the dependence on AV and VV timing in rest condition and obtained more complex contours with many local maxima and no pronounced global maxima in CRT patients.

Although the Whinnett proposal described above is not a perfect Gaussian fit, and differs from patient to patient and differs for individual patients based on heart rate, nonetheless they show the hemodynamic response to the two major CRT timings parameters, the AV delay and VV intervals, and thus remain a useful approach to characterize a CRT patient and to accordingly optimize a CRT device.

However several serious problems are described by Whinnett and Zuber that prevent the production of an easy algorithm to find the optimal AV delay and VV interval per CRT patient. In particular, Whinnett teaches us that the Gaussian fit is hard to obtain with low heart rate, i.e. in rest condition, and Zuber indicates that such as fit may not have a clear global maximum at all. Whinnett teaches that AV and VV optimization is especially important at higher heart rates where CRT patients are more symptomatic and was able to show that at higher heart rate a surface formed from the AV and VV parameters is more easily fitted with a Gaussian and global maxima. However the optimal values at high heart rates are different from those in rest heart rates and since the Gaussian fit at the resting heart rate has no global maxima, the proposal by Whinnett to use the rest condition delays with a correction term for higher rate is not straight forward.

World Intellectual Property Organization Patent Publication WO2005/007075, published to ROM on Jan. 27, 2005 and entitled "Adaptive Resynchronization Therapy System", the entire contents of which are incorporated herein by reference, is addressed to an adaptive CRT device in which the AV delays and the VV intervals are changed online by the implanted device, which act to perform dynamic optimization of the AV delay and the VV intervals. The adaptive CRT device utilizes hemodynamic sensor feedback online and converges to the optimal values using a spiking neurons network and a trial and error gradient ascent algorithm. However, the described adaptive CRT system does not guarantee convergence to optimal pacing therapy.

There is therefore a long felt need to develop a systematic closed loop control system in which the therapeutic stimulation parameters are automatically adjusted so as to deliver safe and optimal performance stimulation therapy. More specifically there is a need to develop a method for online dynamic optimization of the AV delay and VV interval for cardiac resynchronization that will converge to the optimal stimulation timings automatically with any CRT surface that may have in addition to a global optimum also smaller local maxima and the method preferably should deliver optimal therapy at both high heart rates, where CRT patient are more symptomatic, and at lower at rest heart rates.

SUMMARY OF THE INVENTION

Accordingly, it is a principal object of the present invention to overcome the disadvantages of prior art cardiac pacemaker device control systems. This is provided in the present invention by an adaptive control system that learns to deliver optimal stimulation to a subject using a probabilistic replacement scheme that combines direct input from a sensor and an input from an internal lookup table calculated with a QL scheme. In an exemplary embodiment the adaptive control system finds the optimal AV delay and VV interval automatically for high heart rates and specifically in high heart rates where CRT patients are more symptomatic. A random stepping and jump mechanism is integrated within the adaptive CRT control system with the QL scheme to satisfy the exploration condition as described by Watkins and Dayan and thus enables convergence to the global optimal AV delay and VV interval also in the case of complex surfaces that have both local and global maxima.

Certain embodiments provide for a closed loop cardiac pacemaker system comprising: a means for receiving an input from a hemodynamic sensor; an adaptive control system responsive to the hemodynamic sensor with a deterministic master module and a leaning slave module; an interface responsive to the adaptive control system; and a means for receiving and transmitting data from an external programmer. The adaptive control system exhibits four states of operation. In an exemplary embodiment the learning slave module comprises a neural network.

In state one, known as a non-adaptive CRT state, the interface is operated according to programmed stimulation parameters set by a clinician, and the adaptive control system learns to stimulate the heart with the programmed parameters and to associate a temporal pattern received from the hemodynamic sensor with the programmed stimulation parameters.

In state two, known as the gradient ascent (GA) state, the adaptive control system modifies the AV and VV intervals and the leaning module neural network synaptic weights using a reinforcement learning (RL) scheme in order to maximize the immediate reward scalar calculated from the sensor signals received from the hemodynamic sensor.

In state three the highest priority state, known as the QL state, the adaptive control system delivers CRT responsive to both the hemodynamic sensor input gradients and the adaptive control system's predictions using a Q table calculated in accordance with the QL recursive formula.

The adaptive control system switches to a fourth state, known as the FAIL QL state, when the system does not meet a convergence criterion calculated internally or does not meet other pre defined failures criteria. In the FAIL QL state, the adaptive control system continues to deliver CRT as in the QL state, however the synaptic weights adjustment step size is increased as compared to the QL state step size in order to increase the convergence speed of the neural network to the optimal stimulation timings. The adaptive control state maintains the FAIL QL until the algorithm of the adaptive control system converges upon which it reverts to the QL state. Advantageously, the clinician may override the adaptive control system at any time, and the adaptive control system will then switch to a lower priority state, for example the initial non-adaptive CRT state, responsive to the clinician override.

Certain embodiments provide for a cardiac pacemaker control system comprising: a means for receiving input from a hemodynamic sensor; an adaptive control system in communication with the means for receiving input from the hemodynamic sensor; and an interface arranged to provide cardiac stimulation responsive to the adaptive control system; the adaptive control system comprising a learning module operative to converge to patient specific cardiac pacing stimulation timing using a machine learning scheme in cooperation with a probabilistic replacement scheme, the probabilistic replacement scheme arranged to replace inputs from the hemodynamic sensor with online calculated values.

In certain further embodiments the machine learning scheme is a Q-learning scheme. In certain further embodiments, the adaptive control system exhibits a prioritized state machine having a preference to operate in an adaptive state wherein the cardiac pacing stimulation timing is set responsive to the Q-learning or other machine learning scheme and the probabilistic replacement scheme, and further exhibits a non-adaptive state in which input values are implemented for the cardiac pacing stimulation timing, the non-adaptive state being further selected in the event that cardiac pacing stimulation timing of the adaptive state exceeds predetermined parameters or any other predetermined failure condition occurs.

In certain embodiments a replacement rate counter is incremented each time the probabilistic replacement scheme replaces inputs from the hemodynamic sensor with the online calculated values, and wherein the replacement rated counter is set to 0 after expiration of a pre-determined time period. In certain embodiments the machine learning scheme exhibits a closed loop parameter adjustment mechanism arranged to converge the replacement of inputs from the hemodynamic sensor with online calculated values to occur with a predetermined probability.

In certain embodiments the learning module is arranged to calculate a Q-learning table using a recursive Q-learning formula and wherein the learning module comprises a neural network wherein synaptic weights adjustments of the neural network are implemented responsive to both the hemodynamic sensor input and the calculated Q-learning table. In certain embodiments the probabilistic replacement scheme is arranged to explore possible stimulation parameters by a random mechanism. In certain embodiments the interface is an analog interface arranged to drive intra-cardiac leads.

Independently a method of providing cardiac pacing timing is provided for, the method comprising: receiving input from a hemodynamic sensor; and determining cardiac pacing timing responsive to a machine learning scheme in cooperation with a probabilistic replacement scheme, the probabilistic replacement scheme arranged to replace the received inputs with online calculated values.

In certain embodiments the machine learning scheme is a Q-learning scheme. In certain embodiments the determining cardiac pacing timing comprises selecting one of a plurality of states comprising an adaptive state and a non-adaptive state, the selecting exhibiting a preference for the adaptive state, wherein in the adaptive state the cardiac pacing stimulation timing is set responsive to the Q-learning, or other machine learning, and the probabilistic replacement scheme, and wherein in the non-adaptive state input values are implemented for the cardiac pacing stimulation timing, and wherein the non-adaptive state is further selected in the event that cardiac pacing stimulation timing of the adaptive state exceed predetermined parameters or any other predetermined failure condition occurs.

In certain embodiments the method further comprises incrementing a replacement rate counter each time the probabilistic replacement scheme replaces inputs from the hemodynamic sensor with the online calculated values, and setting the replacement rated counter to 0 after expiration of a predetermined time period. In certain embodiments the machine learning scheme exhibits a closed loop parameter adjustment mechanism arranged to converge the replacement of inputs from the hemodynamic sensor with online calculated values to occur with a predetermined probability.

In certain embodiments the determining is accomplished in cooperation with a neural network wherein synaptic weights adjustments of the neural network are implemented responsive to both the hemodynamic sensor input and the calculated Q-learning table. In certain embodiments the probabilistic replacement scheme is arranged to explore possible stimulation parameters by a random mechanism.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DETAILED DESCRIPTION OF THE PREFERRED EMBODIMENTS

Figure 1:
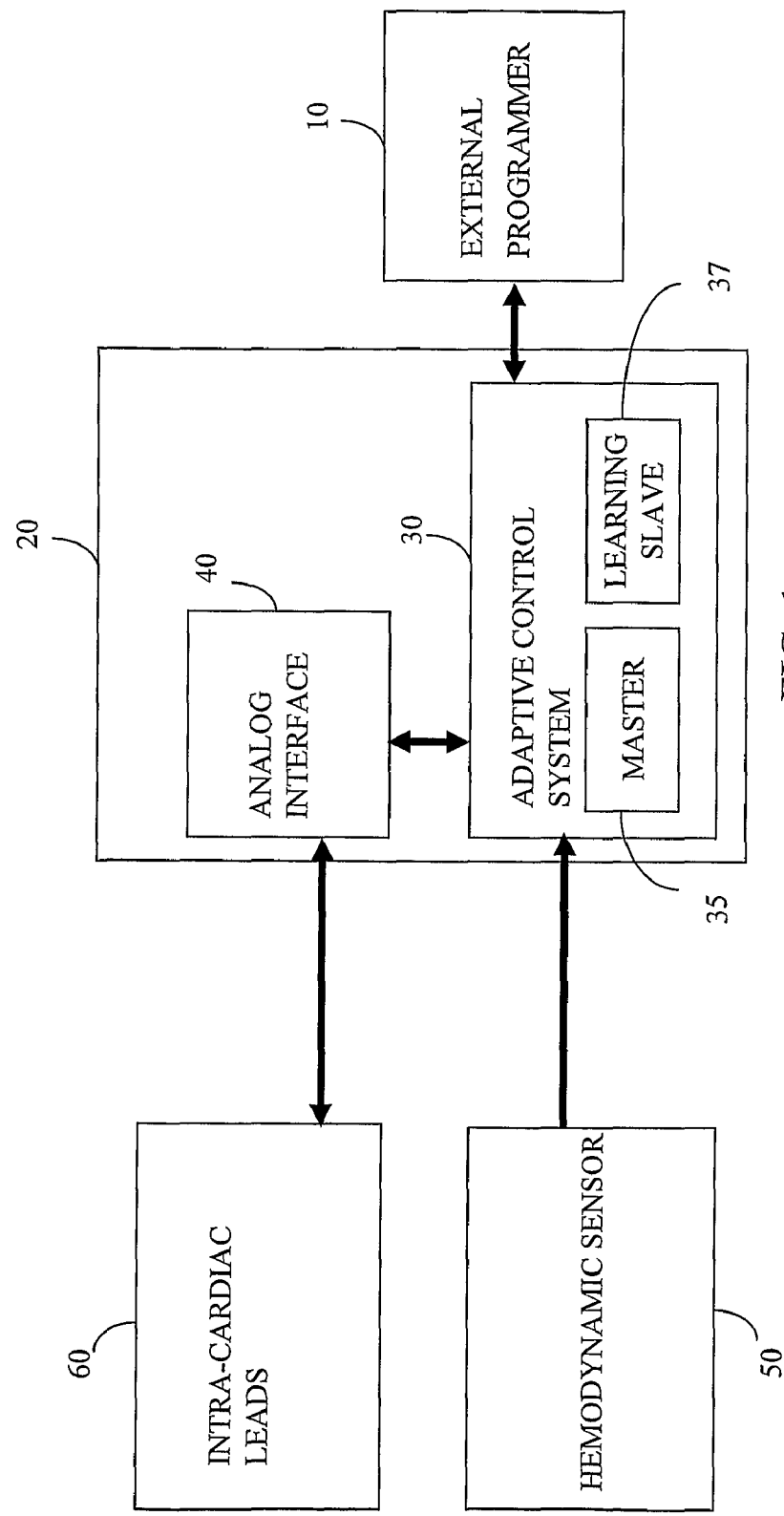
FIG. 1 illustrates a closed loop cardiac bi-ventricular pacemaker system comprising: an adaptive control system; an analog interface responsive to the adaptive control system; a hemodynamic sensor; intra-cardiac leads responsive to the adaptive control system; and an external programmer, according to an exemplary embodiment.

The present embodiments enable an online closed loop cardiac pacemaker control system to achieve optimal and safe performance by learning to deliver the optimal physiologic therapy to cardiac resynchronization therapy (CRT) patients. In certain of the present embodiments a probabilistic replacement scheme is utilized that replaces an input from a hemodynamic sensor with an input from an internal lookup table calculated with an online Q learning scheme. The adaptive control system uses the calculated QL lookup table as an internal representation of its environment. The probability to replace the hemodynamic sensor input with the calculated QL table value each time the stimulation timings are changed depends on the calculated QL table values used here as a confidence measure for the executed stimulation time changes. The probabilistic replacement scheme improves system performance over time and reaches optimal performance even in the face of random noise added to the sensor input.

Advantageously, the closed loop cardiac pacemaker control system according to certain of the present embodiments overcomes the difficulties of sub-optimal CRT due to both sub-optimal lead positioning at implantation and sub-optimal stimulation timings that vary from patient to patient and in the individual patient over their daily life activities.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates a closed loop cardiac bi-ventricular pacemaker system in accordance with an exemplary embodiment comprising: an external programmer 10; a cardiac pacemaker 20 comprising a adaptive control system 30 comprising therein a deterministic master module 35 and a learning slave module 37, and an analog interface module 40; a hemodynamic sensor 50; and intra-cardiac leads 60, typically implemented as three implanted electrodes 60. In one particular embodiment hemodynamic sensor 50 is an implanted sensor, in another particular embodiment hemodynamic sensor 50 is implemented in cooperation with intra-cardiac leads 60, and in another particular embodiment hemodynamic sensor 50 is an external non invasive hemodynamic sensor. A plurality of hemodynamic sensors 50 may be provided without exceeding the scope. Deterministic master module 35 and learning slave module 37 are preferably in all respects similar to the one described in U.S. Patent Application Publication S/N 2006/0235477 entitled "ADAPTIVE RESYNCHRONIZATION THERAPY SYSTEM", published Oct. 19, 2006 to Rom, the entire contents of which is incorporated herein by reference.

Intra-cardiac leads 60 are implanted in the patient body and are connected to analog interface module 40 of cardiac pacemaker 20. Analog interface module 40 is responsive to an output of adaptive control system 30. Adaptive control system 30 is in communication with hemodynamic sensor 50. Adaptive control system 30 is further in communication with external programmer 10, the communication being one of an RF channel, a magnetic channel, or other manual input known to the prior art. In an exemplary embodiment external programmer 10 comprises a display panel, operative to give a visual indication of the changing cardiac pacemaker stimulation parameters output by adaptive control system 30, as will be described further hereinto below, and the response to cardiac stimulation as sensed by hemodynamic sensor 50. External programmer 10 further provides an interface for setting the defined parameters for the non-adaptive operational state of adaptive control system 30 described further hereinto below.

Figure 2:
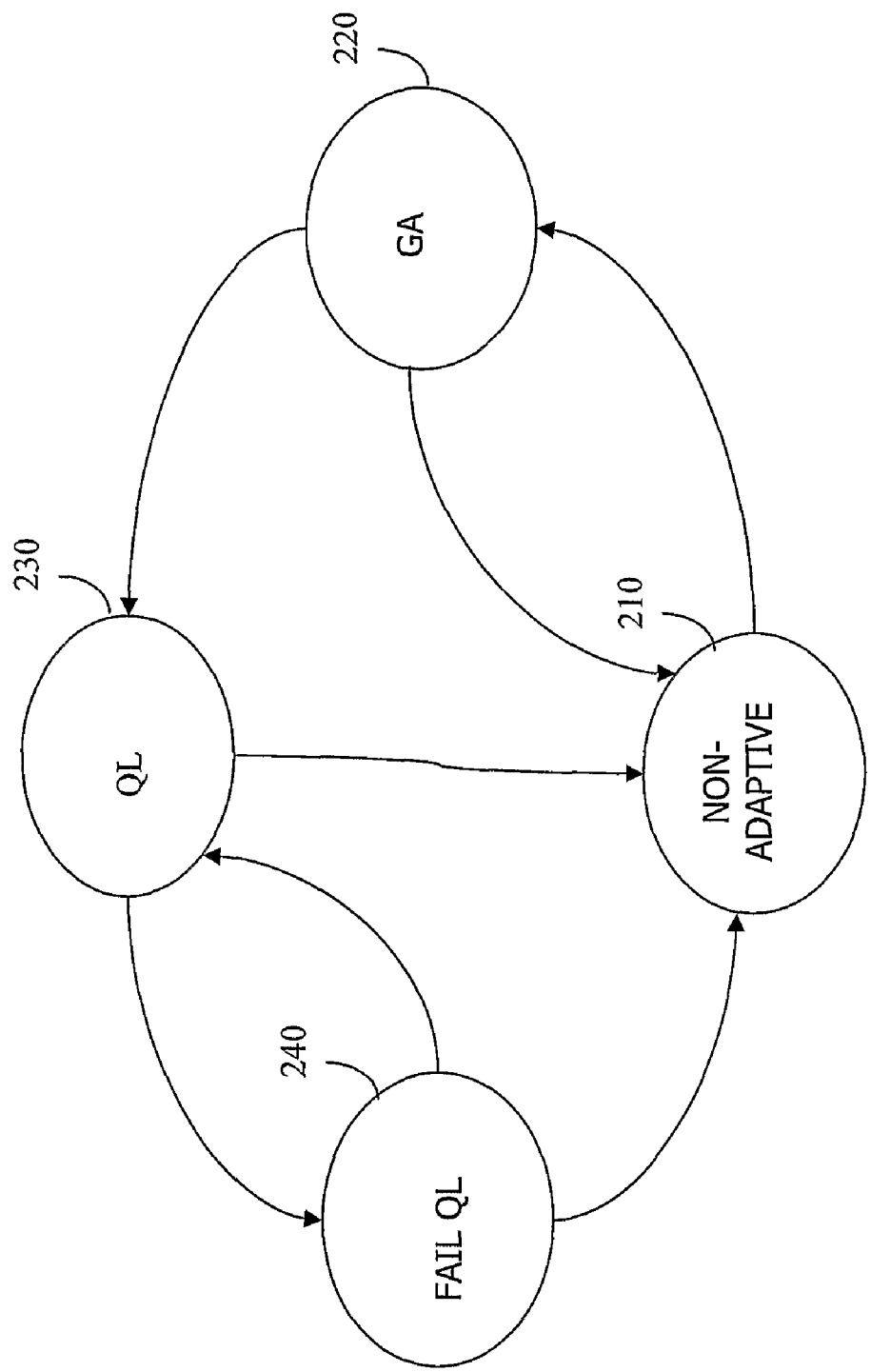
FIG. 2 illustrates a high level block diagram of the states of the adaptive control system of FIG. 1, exhibiting four states of operation with a built in preference for an adaptive QL state according to an exemplary embodiment.

In operation, and with reference to FIG. 2, adaptive control system 30 controls analog interface module 40 to deliver cardiac stimulation therapy via intra-cardiac leads 60 in accordance with the operational states of adaptive control system 30. In particular in a first state, known as a non-adaptive state 210, adaptive control system 30 operates analog interface module 40 responsive to input parameters received from external programmer 10.

Adaptive control system 30 performs a machine learning and in a preferred embodiment a QL scheme and switches between four operating states that will be described further hereinto below. The main state machine shown in FIG. 2, the spiking neurons network of learning slave module 37 and the pattern recognition neural networks and operating modes are similar to those described in World Intellectual Property Organization Patent Publication WO2005/007075, incorporated above by reference.

Adaptive control system 30 receives stimulation parameters from a clinician, through external programmer 10, and in non-adaptive state 210 operates analog interface module 40 as an open loop cardiac pacemaker system known to the prior art. Adaptive control system 30 is further operative, upon convergence of the spiking neurons network of learning slave module 37, to switch to a second state, known as a Gradient Ascent (GA) state 220, in which adaptive control system 30 modifies the stimulation timings, particularly the AV delay and VV interval parameters, using a greedy GA scheme in order to maximize a hemodynamic function calculated online from the output of hemodynamic sensor 50. The stimulation timings are modified within parameters defined by deterministic master module 35, to which learning slave module 37 is responsive. Adaptive control system 30 is further operative, upon convergence of a pattern recognition sigmoid network, to switch to a third state, known as a QL state 230, in which adaptive control system 30 delivers cardiac stimulation therapy via analog interface module 40 using both inputs from hemodynamic sensor 50 and its own predictions based on a QL scheme with a probability that depends on the online calculated Q values, as will be explained further below. A clinician may override adaptive control system 30 at any time via external programmer 10, and in response to such a clinician override input received from external programmer 10, adaptive control system 30 switches to a lower priority state, for example, to the initial non-adaptive state 210. In the event that during QL state 230 the pattern recognition network fails to detect an input pattern, or meets any other pre-defined failure criteria, a FAIL QL state 240 is entered. In FAIL QL state 24 adaptive control system 30 continues to deliver CRT as in QL state 230, however the adjustment step size of the learning algorithm is increased as compared to QL state 230 in order to increase the convergence speed of the neural network. After the re-convergence criterion occurs, adaptive control system 30 transits back to the optimal performance, highest priority QL state 230.

In the event that timings as output by learning slave module 37 exceed a range of timings stored in deterministic master module 35 or another predetermined failure condition occur, deterministic master module 35 resets learning slave module to non-adaptive sate 210.

As indicated above, adaptive control system 30 comprises learning slave module 37, which is preferably implemented as a neural network learning module, and deterministic master module 35 which preferably comprises an algorithmic module. Deterministic master module 35 receiving parameters from learning slave module 37, and provided the parameters are within predetermined boundaries set by the algorithmic module of deterministic master module 35, deterministic master module 35 is operative to control analog interface module 40 to deliver cardiac resynchronization therapy responsive to learning slave module 37.

Preferably, a learning rate parameter that defines the adjustment step size of the spiking neurons synaptic weights of learning slave module 37 depends on the current particular operative state of adaptive control system 30, and its value in each state is a programmable parameter of adaptive control system 30. The learning rate parameter variation in different operative state increases stability and decreases the exploration capability in QL state 230, which is the highest priority state, and furthermore increases the learning rate step size in FAIL QL state 240, thus increasing stability in QL state 230 while increasing exploration capability in FAIL QL state 240.

A responder curve, similar to a responder curve taught in World Intellectual Property Organization Patent Publication WO2006/00165729, published to ROM on Jun. 15, 2006 to ROM and entitled "Optimizing and Monitoring Adaptive Cardiac Resynchronization Therapy Devices", the entire contents of which is incorporated herein by reference, is preferably further used to determine if an effective and optimal lead position site is achieved during the CRT implantation, and if the clinician is not satisfied with the response curve obtained, as viewed on external programmer 10, the clinician can change the lead position during the implantation procedure in order to turn a CRT non-responder patient into a CRT responder, as further described in "Resynchronization and Defibrillation for Heart Failure, A Practical Approach", David L. Hayes et. Al., Blackwell Publishing, 2004.

Figure 3:
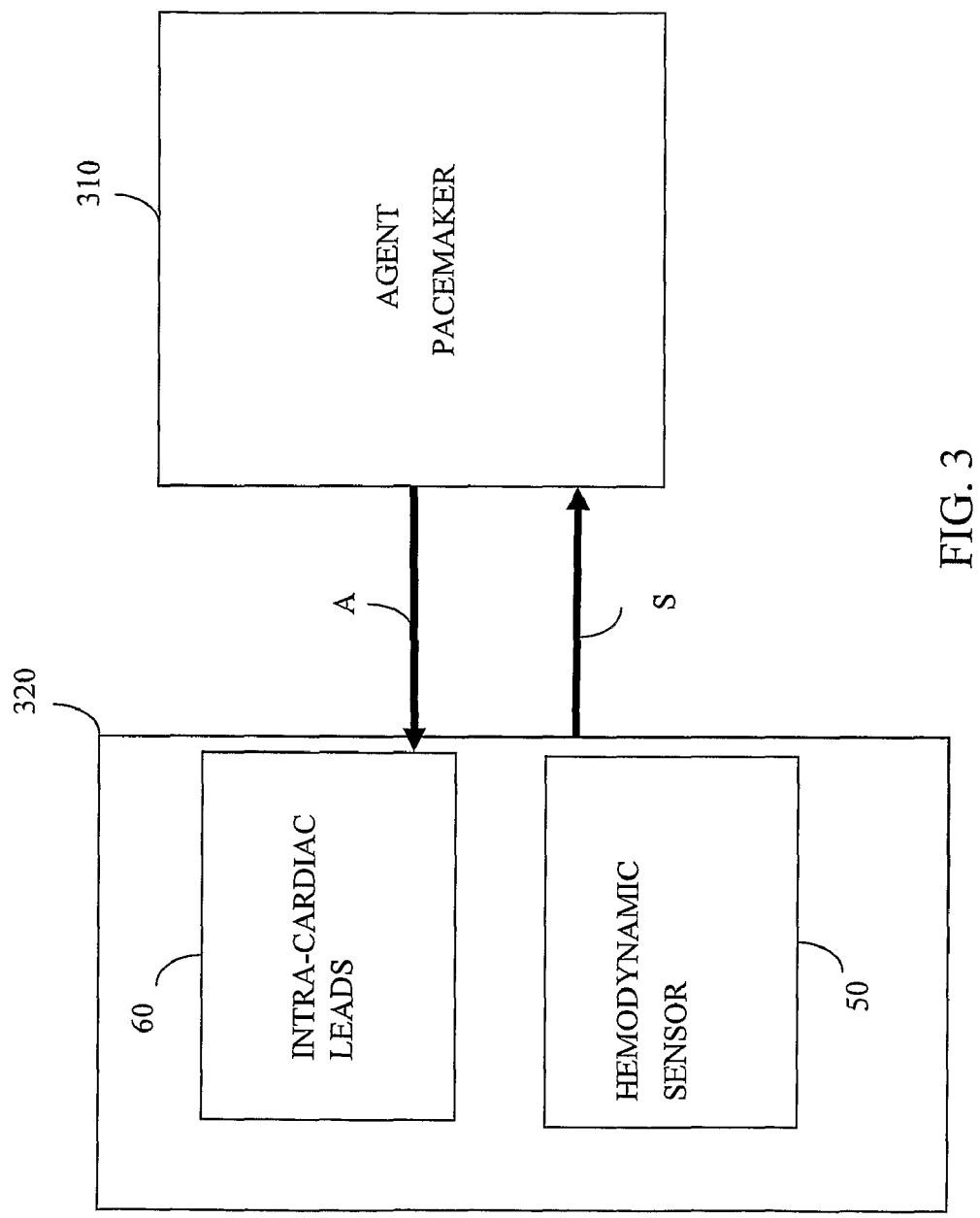
FIG. 3 illustrates a reinforcement learning problem adapted to cardiac pacing in accordance with an exemplary embodiment.

FIG. 3 illustrates an RL problem adaptation to cardiac pacing in accordance with an exemplary embodiment. An agent pacemaker 310, learns optimal behavior through trial-and-error interactions with the dynamic environment of a patient subject heart 320, having associated therewith a hemodynamic sensor 50 and intra-cardiac leads 60, in all respects similar to those described above in relation to FIG. 1. In the standard reinforcement learning model, known to the prior art, as described in "Reinforcement Learning: A Survey", by Leslie P. Kaebling, Michael L. Littman and Anderw W. Moore, Journal of Artificial Intelligence Research 4, 237-285, 1996, agent pacemaker 310 is connected to its environment via perception and action. Agent pacemaker 310 receives as input the current hemodynamic state, denoted S, of the environment from hemodynamic sensor 50. Agent pacemaker 310 then determines the stimulation timing as its possible actions, and outputs the stimulation timing, denoted A, to intra-cardiac leads 60. Output A of agent pacemaker 310 comprises pacing timing and thus changes the state of the heart hemodynamic performance, i.e. the environment state, and the value of this performance change is calculated by agent pacemaker 310 from the resultant change in state S received from hemodynamic sensor 50 as a scalar reinforcement signal. Agent pacemaker task 310 is operative to determine online a particular action A, i.e. pacing timings, that tend to increase the long run sum of values of the scalar reinforcement signal received from hemodynamic sensor 50. Agent pacemaker 310 in particular learns over time by systematic trial and error, guided by one or more RL algorithms. In one particular embodiment agent pacemaker 310 utilizes a QL recursive formula as explained further hereinto below.

Watkins and Dayan as referenced above have taught a QL recursive formula as:

$$Q(S,A)=Q(S,A)+\alpha(R(S,A)+\gamma Q_{max\,A}(S,A)-Q(S,A)) \quad \text{EQ. 1}$$

Where:
A represents the agent action
S represents the environment state
Q(S,A) is the expected discounted reinforcement of taking action A in state S
R(S,A) is the immediate reward response of the environment
$\alpha$ is a small learning rate factor ($\alpha<<1$)
$\gamma$ is the discount factor (smaller then 1)
$Q_{max\,A}$ (S,A) is the learned optimal policy, i.e. the action A that gives the maximum Q value at a given state S out of the possible set of actions.

In the adaptive CRT problem there are two timing parameters that need to be optimized online, the AV delay and VV interval. Hence a Q table is calculated for each configuration of AV and VV values and for each value the possible actions are an increase or decrease in the next cardiac cycle.

$$Q(S,A)=Q(\text{AV Delay},VV \text{ interval},\text{AV Delay}+/-\Delta P,VV \text{ interval}+/-\Delta P) \quad \text{EQ. 2}$$

Where:
A are the pacemaker stimulation timings AV delay and VV interval
S is the heart hemodynamic performance as seen through hemodynamic sensor 50
Q(S,A) is the expected discounted reinforcement calculated table of stimulating with
AV delay and VV intervals, A
R(S,A) is the calculated immediate reward that may be a stroke volume or a systolic blood pressure, without limitation
$Q_{max\,A}$ (S,A) is the Q value for the optimal AV delay and VV intervals.

It is known that by solving the Q learning recursive formula online the agent learns the optimal policy online in a model free reinforcement learning problem with probability of 1 when the action space is visited enough times online meaning that exploration of the action space is sufficient. The advantage of the method taught by Watkins and Dayan as adopted for an agent pacemaker control system herein is that the cardiac pacing timings obtained by solving the recursive formula are guaranteed to converge to the optimal policy, i.e. the optimal stimulation timings that will give maximum hemodynamic performance and without any prior knowledge of the environment, i.e. the detailed cause, physiology of the patient heart disease and the shape of the underlying CRT response surface.

In an exemplary embodiment the probabilistic replacement scheme described below replaces an input from hemodynamic sensor 50 with an input from a lookup table calculated with QL. The probability to replace the sensor input with the calculated QL table value each time an agent action is selected and executed, i.e, the stimulation timings are changed, depends on the calculated QL table values used here as a confidence measure for the executed stimulation time change.

Figure 4:
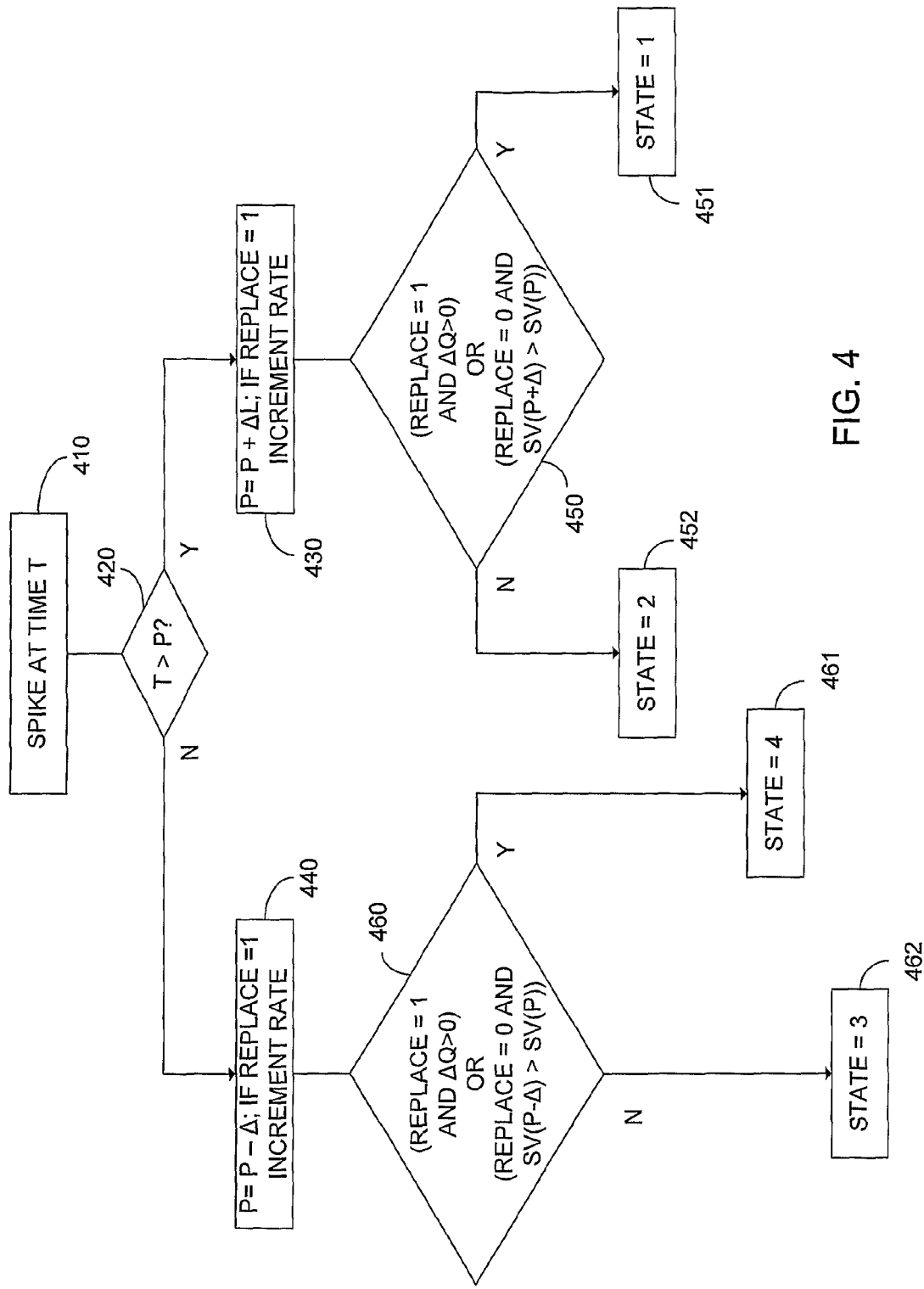
FIG. 4 illustrates a flow diagram for pacing register adjustments and a state selection as part of the probabilistic replacement scheme according to an exemplary embodiment.

FIG. 4 illustrates a flow diagram for the pacing register adjustments and a state selection as part of the reinforcement learning scheme according to an exemplary embodiment and includes a novel important improvement over the flow diagram described in U.S. Patent Application Publication S/N 2006/0235477 incorporated above by reference.

In FIG. 4 the probabilistic replacement scheme and Q learning is added to the adaptive CRT control system flow diagram in an exemplary embodiment of a neural network. The aim of the probabilistic replacement scheme is to replace the input hemodynamic sensor gradients with the calculated online Q lookup table values with a probability that depends on the calculated Q lookup table values. The term online as used herein is meant to include any values that are calculated in real time, i.e. that are calculated responsive to real time events. A replacement rate is calculated and with optimal performance the replacement rate is expected to reach a high value, typically 80% of the executed stimulation timings changes. With the probabilistic replacement scheme, the QL scalar immediate reward value, R(S,A), is either the input hemodynamic sensor gradients, for example stroke volume difference, i.e. SV (P+/−$\Delta$P)−SV (P), or $\Delta$Q, calculated from the Q lookup table values for the executed stimulation timing change, i.e. the pacing register step. With the probabilistic replacement scheme the synaptic weights are modified according to the input hemodynamic sensor gradients or according to the QL values difference ($\Delta$Q) with a probability that depend on $\Delta$Q. The Q Learning lookup table is calculated according to EQ. 2 and stored in the control system memory of adaptive control system 30 each time the stimulation timings are changed, preferably every second cardiac cycle. When the pacing register step executed is a correct step or a wrong step, with high probability, the immediate reward value used in the reinforcement learning flow diagram as shown in FIG. 4 at stages 450 and 460 is replaced with high probability with the sign of the $\Delta$Q and the state selected and the synaptic weights adjustment will follow accordingly. When the confidence measure is low for the executed step, or the QL lookup table value is not selected by a random process, the immediate reward is equal to the hemodynamic sensor gradient, SV (P+/−$\Delta$P)−SV (P), as shown in FIG. 4, stages 450 and 460 as will be explained further below.

Figure 8:
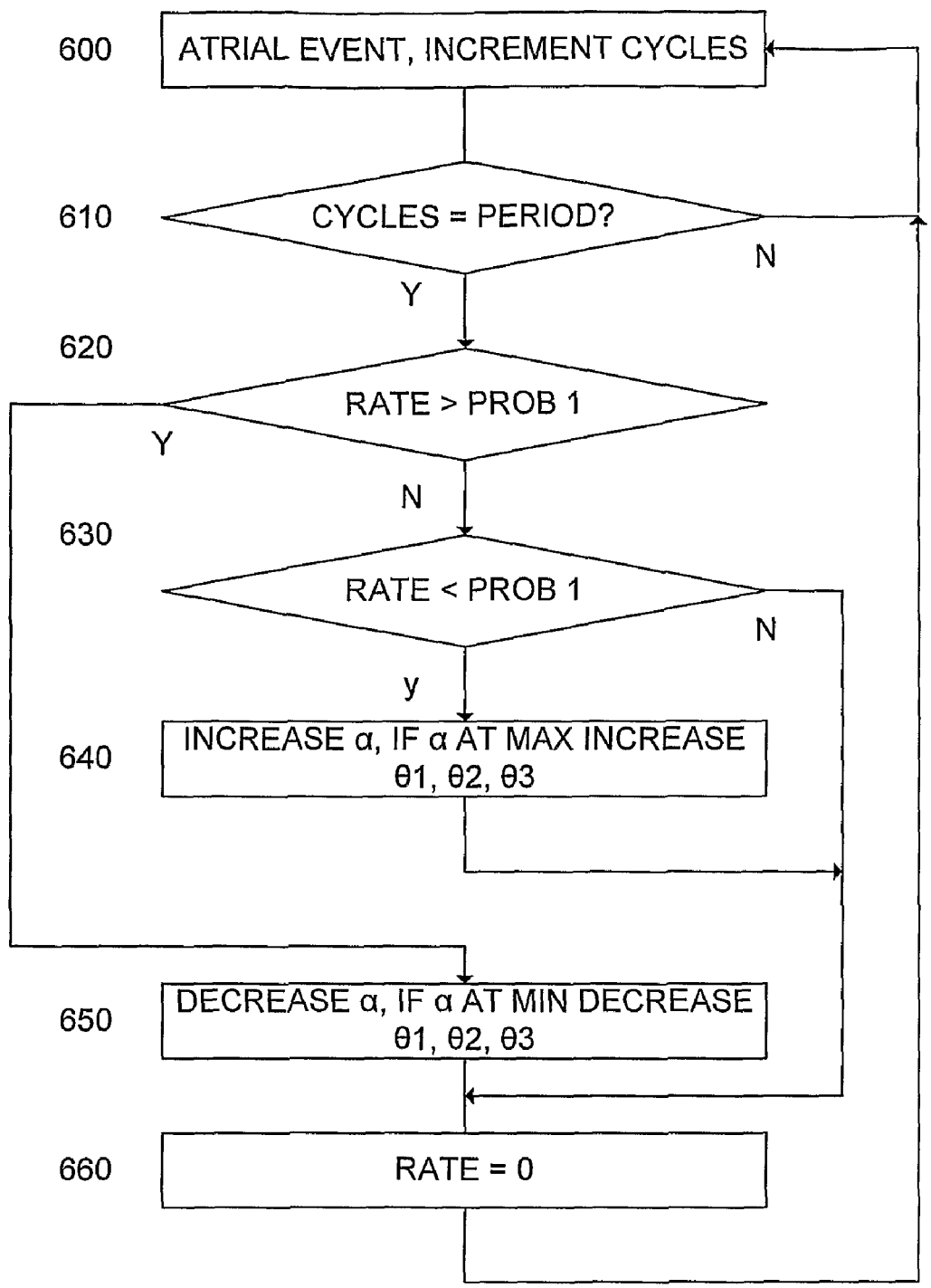
FIG. 8 illustrates a high level flow chart of parameter adjustment according to an exemplary embodiment.

Referring now to FIG. 4 in detail, in stage 410, at the first cardiac cycle, the integrate-and-fire (I&F) neuron firing timing spike occurs at time T, and the spike timing T is stored. In particular, the time T is defined relative to a sensed or paced atrial event sensed by one of intra-cardiac leads 60. In stage 420, time T of stage 410 is compared with a value stored at a pacing register P, the value being the actual pacing time. It is to be noted that the flow of FIG. 4 occurs separately for both the timing of the AV delay and the VV interval. Note that the relative timing of the spike timing relative to the pacing register value is a random process and hence the result of stage 420 is random. In the event that T>P, in stage 430 the pacing register value is incremented by a programmable value $\Delta$P, i.e. P=P+$\Delta$ and the replace condition, defined further below and denoted REPLACE, is calculated and in the event that REPLACE is true, i.e. equal to 1, a replacement rate counter, denoted RATE, and described further in relation to FIG. 8, is incremented. In the next cardiac cycle, responsive to pacing P+Δ, a new input from hemodynamic sensor 50 is received.

In stage 450, when REPLACE is true, i.e. equal to 1, the QL lookup table described above in relation to EQ. 2 is used to substitute for the input from hemodynamic sensor 50 for the cardiac cycle with pacing P+Δ and when ΔQ>0 using the input from the QL lookup table STATE 1 is entered in stage 451. When ΔQ<0 using the input from the QL lookup table STATE 2 is entered in stage 452.

In the event that in stage 450 the replace condition is false, i.e. equal 0, the input from hemodynamic sensor 50 is used and SV (P+Δ), which is the stroke volume calculated from the hemodynamic sensor input with AV delay=P+Δ, is compared with SV (P). When SV (P+Δ) is greater than SV (P), i.e. the stroke volume is improved by increasing the stimulation time, STATE 1 is entered in stage 451. In the event that SV (P+Δ) is not greater than SV (P), i.e. the stroke volume has decreased, STATE 2 is entered in stage 452.

In the event that in stage 420, T is not greater than P, i.e. T<=P, in stage 440 the pacing register value is decremented by a programmable value ΔP, i.e. P=P−Δ, REPLACE, is calculated and in the event that REPLACE is true, i.e. equal to 1, replacement rate counter RATE is incremented. In the next cardiac cycle, responsive to pacing P−Δ, a new input from hemodynamic sensor 50 is received.

In stage 460, when REPLACE is true, i.e. equal to 1, the QL lookup table described above in relation to EQ. 2 is used to substitute for the input from hemodynamic sensor 50 for the cardiac cycle with pacing P−Δ and when ΔQ>0 using the input from the QL lookup table STATE 4 is entered in stage 461. When ΔQ<0 using the input from the QL lookup table STATE 3 is entered in stage 462.

In the event that in stage 460, when the replace condition is false, i.e. equal 0, the input from hemodynamic sensor 50 is used and SV (P−Δ), which is the stroke volume calculated from the hemodynamic sensor input data with AV delay=P−Δ, is compared with SV (P). In the event that SV (P−Δ) is greater than SV (P), i.e. the stroke volume has improved, STATE 4 is entered in stage 461. In the event that SV (P−Δ) is not greater than SV (P), i.e. the stroke volume has decreased, STATE 3 is entered in stage 462

The replacement condition depends on the calculated QL lookup table for the executed step, on three programmable confidence thresholds, on a random selection mechanism and on the control system states shown in FIG. 2. Three programmable thresholds are defined: θ1, θ2 and θ3, which are set to control the statistical response as described below, and respective factors are set to be used in combination with a random number generator, respectively denoted PROB1, PROB2 and PROB3. In an exemplary embodiment PROB1 is set to 80%, PROB2 is set to 70% and PROB3 is set to 50%. ΔQ is withdrawn from the QL lookup table and if |ΔQ| is bigger than θ1, the results of the random number generator are compared with PROB1, such that with PROB1 REPLACE=1. When |ΔQ| is smaller than θ1 and bigger than θ2, the results of the random number generator are compared with PROB2, such that with PROB2 REPLACE=1. When |ΔQ| is smaller than θ3, the results of the random number generator are compared with PROB3, such that with PROB3 REPLACE=1. In non-adaptive state 210 and in GA state 220, both of FIG. 2, the replacement mechanism is disabled and REPLACE is set to 0. Thus, non-adaptive state 210 and GA state 220, responsive to stages 450 and 460 of FIG. 4 the synaptic weights adjustments will be performed according to the input sensor gradient. In QL state 230 and in FAIL QL state 240 the value of REPLACE is 0 or 1 depending on the QL lookup table as explained above, and when it is true, i.e. REPLACE=1, the synaptic weights adjustments will be performed according to the sign of ΔQ as shown in stages 450 and 460, respectively. In FAIL QL state 240 the synaptic weights adjustment step size, denoted ΔW in FIG. 5 is increased relative to the adjustment step size of QL state 230 in order to increase the convergence speed of the neural network to the optimal stimulation timings, i.e. the spike timing T.

Thus, as explained above, PROB1, PROB2 and PROB3, respectively associated with θ1, θ2 and θ3 are used as a confidence measure calculated from the QL lookup table and each time the replacement condition is true a replacement rate counter, denoted RATE is incremented. RATE is compared over a predetermined number of cardiac cycles, typically 2000 cardiac cycles, to define the effectiveness of the probabilistic replacement scheme as explained further below.

In clarification of the operation of FIG. 4, it is to be understood that incrementing or decrementing P, as described above in relation to stages 430 and 440, respectively, results in agent pacemaker 310 of FIG. 3 setting an updated stimulation timings for the next cardiac cycle. As a result a new value for the hemodynamic response will be calculated using data received from hemodynamic sensor 50. The measured gradient difference, SV (P+/−ΔP)−SV (P), is defined as the immediate reward scalar in the recursive formula described above in relation to EQ. 1, i.e. R(S,A), since for the reinforcement learning scheme of the present embodiments SV (P) is the stroke volume calculated from the hemodynamic sensor 50 input data with AV delay=P and SV (P+/−ΔP) is the stroke volume calculated from the hemodynamic sensor 50 input data with AV delay=P+/−ΔP after the pacing register was updated.

Figure 5:
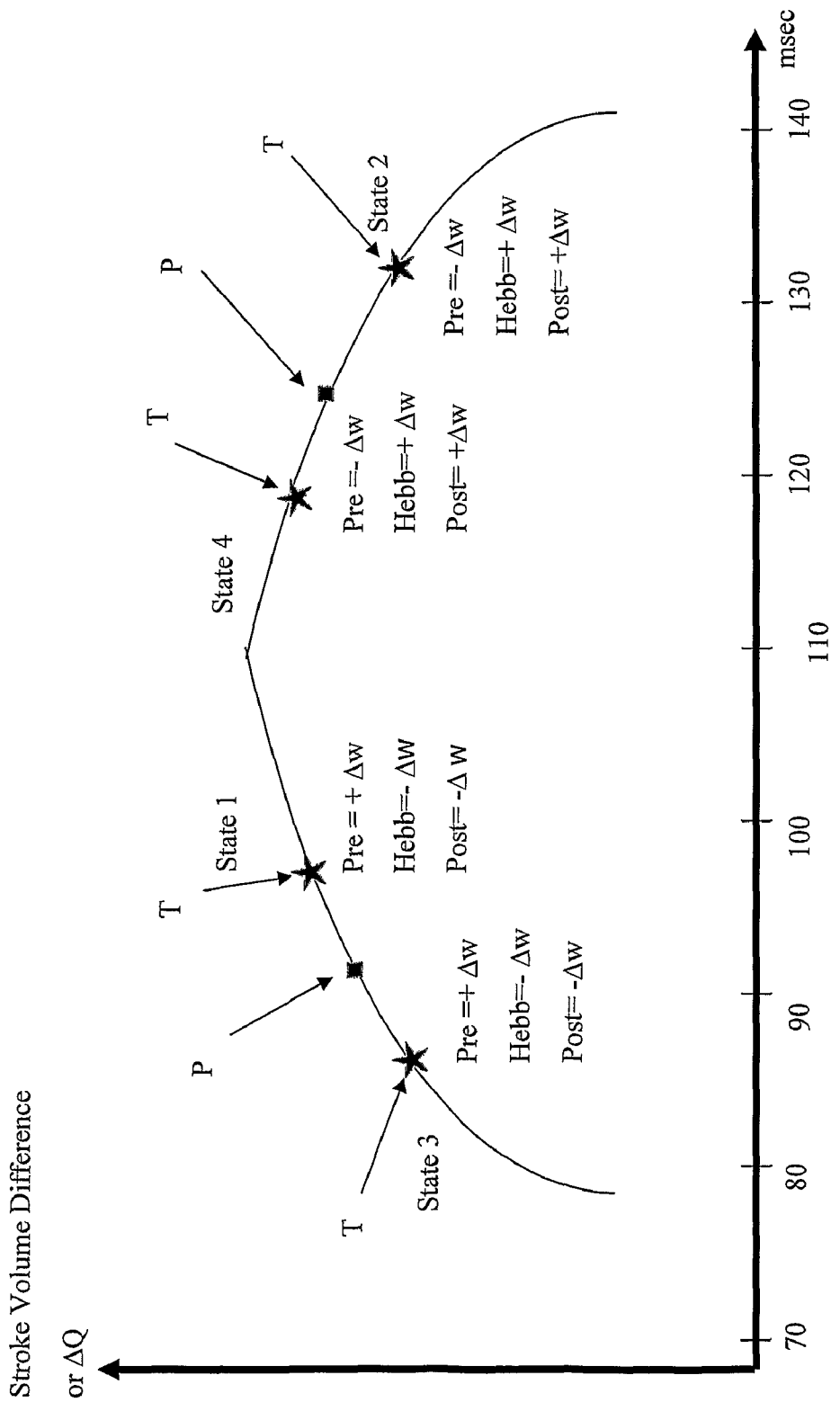
FIG. 5 illustrates a flow diagram for neural network synaptic weight adjustments as part of the present reinforcement learning scheme according to an exemplary embodiment.

FIG. 5, which is in all respects similar to one shown in World Intellectual Property Organization Patent Publication WO2005/007075 incorporated above, shows how the four states 1-4, as described above are used to define the sign of the synaptic weights adjustments in each synapse of learning slave module 37, in which the x-axis represents time in milliseconds, and the y-axis represents the stroke volume difference or ΔQ according to the replacement condition value described above in relation to FIG. 4. The synaptic states, PRE-HEBB, HEBB and POST-HEBB defined in WO 2005/007075, are stored internally in each synapse of agent pacemaker 310, or more particularly in learning slave module 37. Each of these states are a measure of the timing of the post synaptic time relative to the pre-synaptic excitation and hence the learning rule adjustments are specific to each synapse and follow the hemodynamic sensor gradients.

With the probabilistic replacement scheme explained above the synaptic weights adjustments learning rule is modified according to either the measured input hemodynamic sensor gradients or the calculated Q values difference, ΔQ, with a probability that depend on the absolute value of the calculated ΔQ.

The α parameter of EQ. 1 determines the learning rate of the QL scheme. With a high value of α the QL table will converge faster however in noisy environment a large α parameter will cause instability in the QL scheme. Hence an automatic regulation scheme of α, via the θ1, θ2, and θ3 parameters, is used to ensure proper performance. The regulation scheme is based on the replacements rate where the maximal replacement rate allowed, i.e. the value PROB1 associated with θ1, achieves are replacement rate, RATE, of PROB1. Thus, in the exemplary embodiment where PROB1 is 80%, this means that θ1 is varied such that RATE converges to PROB1, which means that 80% of the decisions made by the adaptive control system 30 over the predetermined number of cardiac cycles are done according to the calculated Q values replacing the measured sensor gradients. The high limit parameter θ1 is a measure of how effective the QL replacement scheme will be.

FIG. 8 illustrates a high level flow chart of parameter adjustment according to an exemplary embodiment. In stage 600 an atrial event or other event consonant with the number of cardiac cycles occurs, and a counter denoted CYCLES is incremented. In stage 610 the value of CYCLES is compared with predefined value PERIOD, which as described above is typically 2000 cycles. If CYCLES is not equal to period, i.e. less than the predefined number of cycles has occurred, stage 600 is again performed.

In the event that in stage 610 CYCLES is equal to PERIOD, in stage 620 the value of RATE normalized by CYCLES, i.e. the actual replacement rate as described above in relation to FIG. 4 is compared with value PROB1. In the event that RATE normalized by CYCLES is greater than PROB1, i.e. the replacement rate is greater than the target replacement rate, in stage 650 the value for α is reduced, preferably by a predetermined step size, provided that α may not be reduced below a predetermined minimum level. In the event that α is at the predetermined minimum value, programmable thresholds θ1, θ2 and θ3 are reduced preferably by a predetermined step size. In stage 660, counter RATE is reset to zero, and stage 600 is again performed.

In the event that in stage 620 RATE normalized by CYCLES is not greater than PROB1, in stage in stage 630 the value of RATE normalized by CYCLES is again compared with value PROB1. In the event that RATE normalized by CYCLES is less than PROB1, i.e. the replacement rate is less than the target replacement rate, in stage 640 the value for α is increased, preferably by a predetermined step size, provided that α may not be increased above a predetermined maximum level. In the event that α is at the predetermined maximum level, programmable thresholds θ1, θ2 and θ3 are increased preferably by a predetermined step size. In stage 660, counter RATE is reset to zero, and stage 600 is again performed. In the event that in stage 630 RATE is not less than PROB1, thus RATE is equal to PROB1, no change in programmable thresholds θ1, θ2 and θ3 and α is required and in stage 660 counter RATE is reset to zero, and stage 600 is again performed.

The number of replacements performed in a period depends on the αvalue and on the 3 threshold values θ1, θ2 and θ3 that are used in the probabilistic mechanism of the Q replacements. The α parameter is initially set to a low value. Typically 0.02 and is incremented slowly if the replacement rate is below the programmed high limit until it reach the maximal value allowed for α, typically 0.1. When the replacement rate is higher then the maximal value allowed α is decreased until it reaches the lower limit.

Thus, the three programmable thresholds θ1, θ2, and θ3 regulation scheme depends on α and on the replacement rate. The initial programmable thresholds values for θ1, θ2, and θ3 are set to low values, typically 10, 20 and 30, respectively. When α is minimal and the replacement rate is still too high, the thresholds will be decremented gradually until the replacement rate is lowered by the method of FIG. 8. When α is maximal, and the replacement rate is still too low the thresholds will be incremented. The aim of both α and the 3 thresholds values regulation is to maintain a steady replacement rate close to the maximal value programmed, as set by PROB1.

Whinnett et al and Zuber et have argued that at low heart rates the response of CRT patients to pacing with different AV delay and VV intervals is less then expected at higher heart rates which makes the problem of finding the optimal AV and VV delays at rest in a follow up examination a more difficult task for the clinician. In order to increase exploration capabilities of the QL replacement scheme of the present application and to meet the Watkins and Dayan condition for the QL recursive formula proof of convergence to the optimal policy, a random jump mechanism is added to the QL replacement scheme. The random jump mechanism is added in order to increase exploration capability and also to allow escape from local maxima and any flat regions in the CRT response surface as measured with hemodynamic sensor 50. The random jump mechanism depends on the QL lookup table where a jump will occur with higher probability if the QL difference is above a threshold in the direction predicted by the QL lookup table and with smaller probability in the opposite direction. Typically the jump step is of 40 msec where the normal step is 5 msec. Typically the random jumps occur once every 2000-4000 cardiac cycles.

In summary of FIGS. 4, 5 and 8, a new and improved flow diagram with a probabilistic replacement scheme based on QL is presented. The synaptic weights adjustments are advantageously accomplished according to either the sensor input or the calculated QL table, and a random jump is preferably further implemented.

Figure 6A:
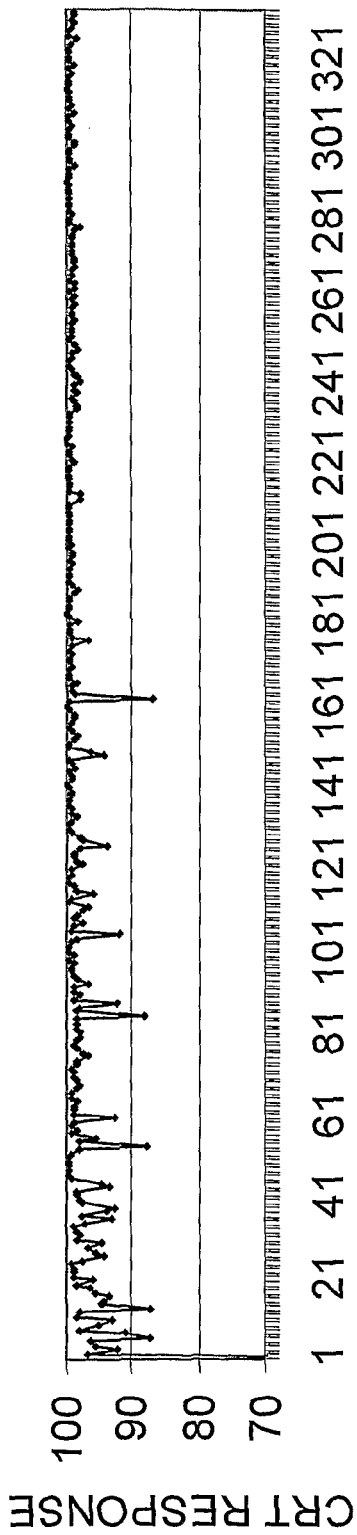
FIGS. 6A and 6B show the convergence to optimal performance in a noisy environment with QL.
Figure 6B:
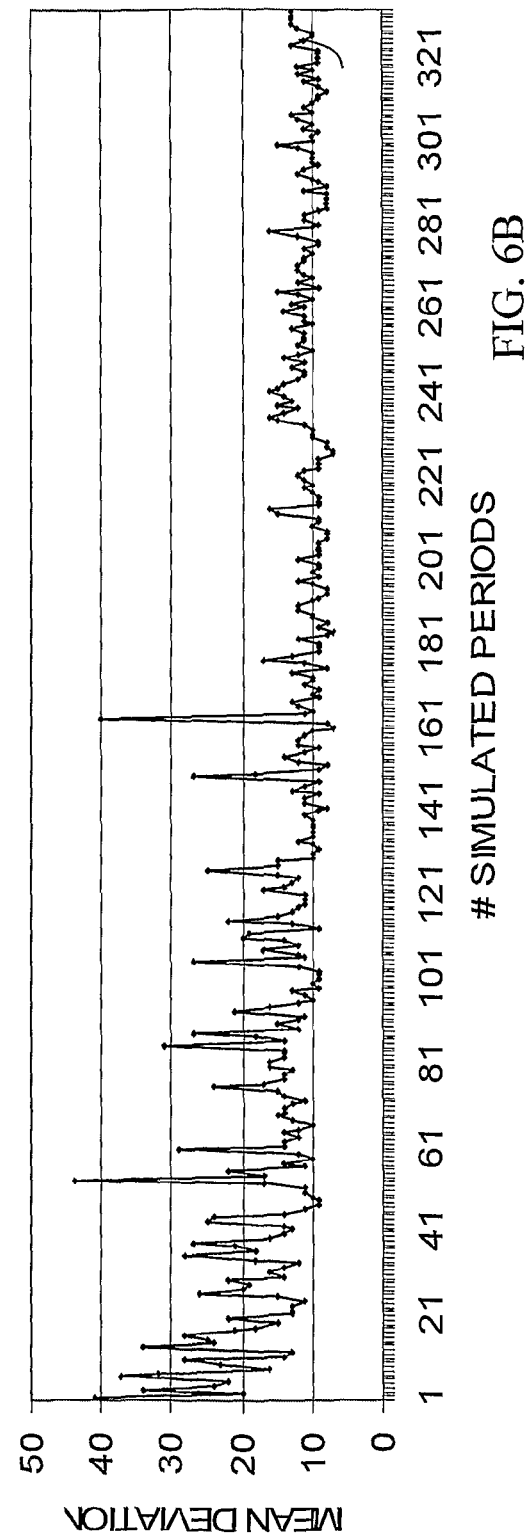

FIGS. 6A and 6B show the convergence to optimal performance of the adaptive control system of the present embodiments with a random noise inserted in the signal from hemodynamic sensor 50. FIG. 6A shows the normalized CRT response calculated during a long simulation with periodic changes in the heart rate between 70 BPM to 110 BPM, where the x-axis represents simulation periods and the y-axis represents normalized CRT response. Before convergence of the QL replacement scheme, i.e. until approximately 170 periods, the performance is below 80% and unstable, with lower performance periods from time to time, while after about 170 simulation periods the performance is almost optimal with very little deviation although random noise levels inserted to input from hemodynamic sensor 50 was kept high during all the simulation.

FIG. 6B shows the mean deviation from the optimal AV delay during the simulation, wherein the x-axis represents simulation periods and the y-axis represents mean deviation in milliseconds. As described above in relation to FIG. 6A after the QL replacement scheme of the subject application has converged after about 170 periods the deviation from optimal values is negligible, about 10 msec, with small deviations, while before convergence the mean deviation due to the strong random noise was about 30 to 40 msec.

The normalized CRT response shown in FIGS. 6A and 7, to be described further hereinto below, is the normalized average of the sum of the CRT responses received during a predetermined simulation period, where the predetermined simulation period represents 2000 cardiac cycle. In particular:

The accumulated CRT Response=$1/2000*\Sigma_1^{2000}$ CRT Response($i$);

The normalize performance is calculated according to:

Normalized CRT Response=[Accumulated CRT Response−CRT Response Min]/[CRT Response Max−CRT Response Min]*100; and CRT Response Min=CRT Response (AV=60, $VV$=0) and CRT Response Max=CRT Response (AV=160, $VV$=0).

Figure 7:
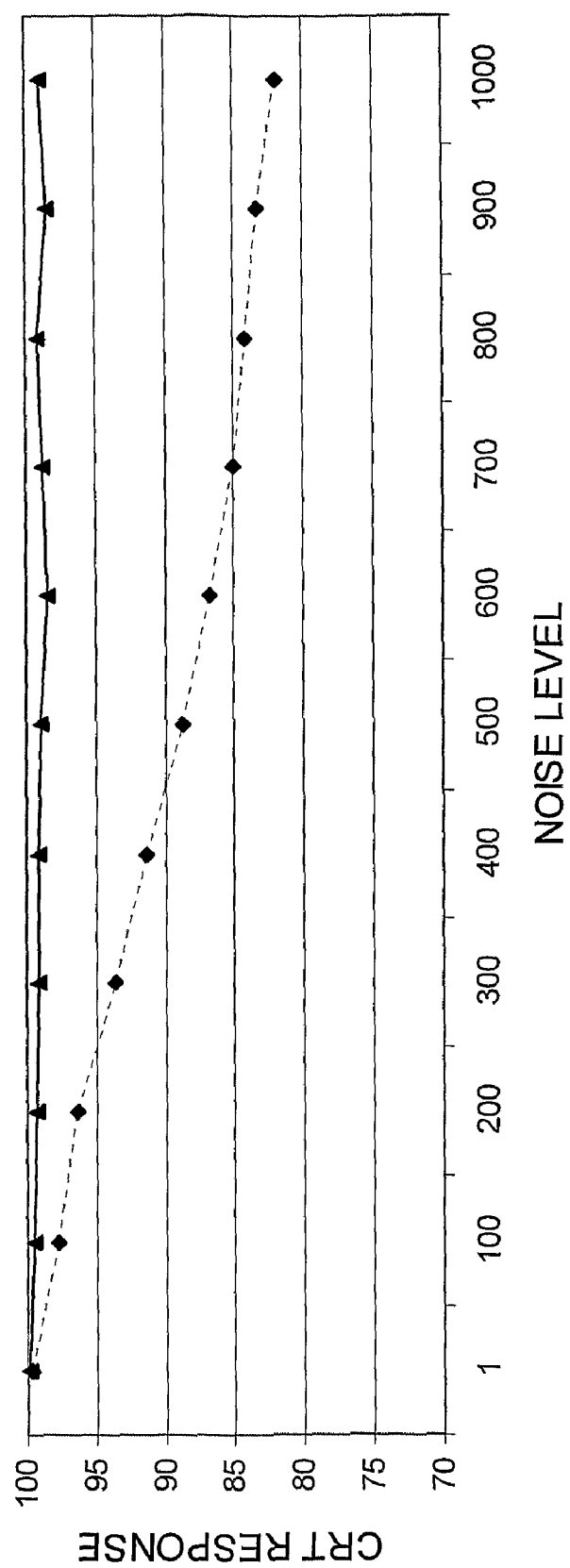
FIG. 7 exhibits a simulation comparing QL replacement performance with a gradient ascent scheme performance in a noisy environment.

FIG. 7 shows performance of a CRT device exhibiting adaptive control system 30 with QL according to an exemplary embodiment compared a similar CRT device operating according to a gradient ascent scheme with different noise levels added to the hemodynamic sensor input during the simulation. In particular, the x-axis represents the added noise level in arbitrary units and the y-axis represents normalized response. The response curve exhibiting triangular data points represents the performance of the CRT device exhibiting adaptive control system 30 with QL, and the response curve exhibiting the diamond shaped data points represents the performance of the CRT device exhibiting the gradient ascent scheme. FIG. 7 shows that performance without QL deteriorates linearly with growing noise, whereas performance with QL is nearly unaffected by the varying noise level. Since the CRT responses is proportional to patient cardiac output, FIG. 7 shows that QL increases the cardiac output of the CRT patient and brings it to optimal values, thus achieving a major goal of CRT.

As shown in FIGS. 6A and 6B the normalized CRT response improves as the simulation periods continue and reach the optimal values as adaptive control system 30 learns to deliver pacing with optimal AV delay and VV intervals in rest and exercise conditions and the overall system performance improves and reaches the optimal system performance irrespective of noise in the input from hemodynamic sensor 50.

Adaptive control system 30 including the QL replacement scheme of the present embodiments may be implemented in hardware as an ASIC processor or as a block in a system on a multi-function processing device. Adaptive control system 30 may also be implemented with software using a general purpose micro-controller of a pacemaker device.

Adaptive control system 30 using the present invention probabilistic replacement scheme can be implemented with other machine learning schemes and is not limited to the Watkins and Dayan Q-learning scheme described. In particular machine learned schemes including, without limitation all reinforcement learning (RL) schemes and more generally other adaptive control methods may be utilized to replace the QL scheme without exceeding the scope.

Advantageously, a cardiac pacemaker control system implemented as described above learns to deliver optimal and safe resynchronization therapy tailored to each CRT patient using the QL replacement scheme.

Another advantage of a cardiac pacemaker control system implemented as described above is that it learns to deliver optimal and safe CRT using a prioritized state machine, having a built in preference to operate in the QL state, that brings optimal performance while exhibiting an initialization and fallback state which enables a clinician to input pre-programmed stimulation parameters, in particular an AV delay and VV interval.

Another advantage of a cardiac pacemaker control system implemented as described above is that the use of the QL lookup table as an internal representation of the system environment to replace the measured sensor data with a probabilistic scheme succeeds in improving performance over time to reach optimal performance in a noisy environment.

Another advantage of a cardiac pacemaker control system implemented as described above is that it converges automatically to the optimal AV delay and VV interval at both lower heart rates and more significantly at higher heart rates where CRT patient are more symptomatic and need higher cardiac output.

Another advantage of a cardiac pacemaker control system implemented as described above is that it converges automatically to the global optimal AV delay and VV interval even in the case when there are smaller local maxima in the CRT surface.

Another advantage of a cardiac pacemaker control system implemented as described above is that it enables validation of optimal lead positioning during a CRT device implantation using the responder curve, thus enabling a clinician to turn a non-responder CRT patient to a CRT responder.

Another advantage of a cardiac pacemaker control system implemented as described above is that optimal CRT will improve acute patient hemodynamic response to pacing thus improving even acute CRT patients with an increased cardiac output and stroke volume.

Another advantage of a cardiac pacemaker control system implemented as described above is that optimal CRT is expected to improve long term chronic hemodynamic performance with an expected increase in the reverse modeling phenomenon with expected reduction in left ventricle (LV) size and improvements in LV function.

In summary, a cardiac pacemaker control system implemented as described above overcomes the difficulties of sub-optimal, non-optimized CRT therapy due to both sub-optimal lead positioning and the lack of a handy and systematic patient follow-up routine that enables optimizing CRT device stimulation timings manually.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

I claim:

1. A cardiac pacemaker control system comprising:
a means for receiving input from a hemodynamic sensor;
an adaptive control system in communication with said means for receiving input from said hemodynamic sensor; and
an interface arranged to provide cardiac stimulation responsive to said adaptive control system;
said adaptive control system comprising a learning module arranged to converge to patient specific cardiac pacing stimulation timing using a machine learning scheme in cooperation with a probabilistic replacement scheme, said probabilistic replacement scheme arranged to replace inputs from said hemodynamic sensor with online calculated values.

2. A cardiac pacemaker control system according to claim 1, wherein said machine learning scheme is a Q-learning scheme.

3. A cardiac pacemaker control system according to claim 2, wherein said adaptive control system exhibits a prioritized state machine having a preference to operate in an adaptive state wherein said cardiac pacing stimulation timing is set responsive to said Q-learning and said probabilistic replacement scheme, and further exhibits a non-adaptive state in which input values are implemented for said cardiac pacing stimulation timing, said non-adaptive state being further selected in the event that cardiac pacing stimulation timing of said adaptive state exceeds predetermined parameters or any other predetermined failure condition occurs.

4. A cardiac pacemaker control system according to claim 1, wherein said adaptive control system exhibits a prioritized state machine having a preference to operate in an adaptive state wherein said cardiac pacing stimulation timing is set responsive to said machine learning scheme and said probabilistic replacement scheme, and further exhibits a non-adaptive state in which input values are implemented for said cardiac pacing stimulation timing, said non-adaptive state being further selected in the event that cardiac pacing stimulation timing of said adaptive state exceed predetermined parameters or any other predetermined failure condition occurs.

5. A cardiac pacemaker adaptive control system according to claim 1, wherein a replacement rate counter is incremented each time said probabilistic replacement scheme replaces inputs from said hemodynamic sensor with the online calculated values, and wherein said replacement rated counter is set to 0 after expiration of a pre-determined time period.

6. A cardiac pacemaker adaptive control system according to claim 1, wherein said machine learning scheme exhibits a closed loop parameter adjustment mechanism arranged to converge said replacement of inputs from said hemodynamic sensor with online calculated values to occur with a predetermined probability.

7. A closed loop cardiac pacemaker system according to claim 1, wherein said learning module is arranged to calculate a Q-learning table using a recursive Q-learning formula and wherein said learning module comprises a neural network wherein synaptic weights adjustments of said neural network are implemented responsive to both said hemodynamic sensor input and said calculated Q-learning table.

8. A cardiac pacemaker control system according to claim 1, wherein said probabilistic replacement scheme is arranged to explore possible stimulation parameters by a random mechanism.

9. A cardiac pacemaker control system according to claim 1, wherein said interface is an analog interface arranged to drive intra-cardiac leads.

10. A method of providing cardiac pacing timing, the method comprising:
receiving input from a hemodynamic sensor;
determining cardiac pacing timing responsive to a machine learning scheme in cooperation with a probabilistic replacement scheme, said probabilistic replacement scheme arranged to replace said received inputs with online calculated values; and
providing cardiac stimulation responsive to said determined cardiac pacing timing.

11. A method according to claim 10, wherein said machine learning scheme is a Q-learning scheme.

12. A method according to claim 11, wherein determining cardiac pacing timing comprises selecting one of a plurality of states comprising an adaptive state and a non-adaptive state, said selecting exhibiting a preference for the adaptive state, wherein in said adaptive state said cardiac pacing stimulation timing is set responsive to said Q-learning and said probabilistic replacement scheme, and wherein in said non-adaptive state input values are implemented for said cardiac pacing stimulation timing, and wherein said non-adaptive state is further selected in the event that cardiac pacing stimulation timing of said adaptive state exceed predetermined parameters or any other predetermined failure condition occurs.

13. A method according to claim 10, wherein determining cardiac pacing timing comprises selecting one of a plurality of states comprising an adaptive state and a non-adaptive state, said selecting exhibiting a preference for the adaptive state, wherein in said adaptive state said cardiac pacing stimulation timing is set responsive to said machine learning and said probabilistic replacement scheme, and wherein in said non-adaptive state input values are implemented for said cardiac pacing stimulation timing, and wherein said non-adaptive state is further selected in the event that cardiac pacing stimulation timing of said adaptive state exceed predetermined parameters or any other predetermined failure condition occurs.

14. A method according to claim 10, further comprising incrementing a replacement rate counter each time said probabilistic replacement scheme replaces inputs from said hemodynamic sensor with the online calculated values, and setting said replacement rated counter to 0 after expiration of a pre-determined time period.

15. A method according to claim 10, wherein said machine learning scheme exhibits a closed loop parameter adjustment mechanism arranged to converge said replacement of inputs from said hemodynamic sensor with online calculated values to occur with a predetermined probability.

16. A method according to claim 10, wherein said determining is accomplished in cooperation with a neural network wherein synaptic weights adjustments of said neural network are implemented responsive to both said hemodynamic sensor input and said calculated Q-learning table.

17. A method according to claim 10, wherein said probabilistic replacement scheme is arranged to explore possible stimulation parameters by a random mechanism.

* * * * *